US00PP13767P39

(12) United States Plant Patent
Pieters

(10) Patent No.: US PP13,767 P3
(45) Date of Patent: May 6, 2003

(54) CHRYSANTHEMUM PLANT NAMED 'GEDI ONE FRI'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,957

(22) Filed: Jun. 4, 2001

(65) Prior Publication Data

US 2002/0199227 P1 Dec. 26, 2002

(51) Int. Cl.[7] ..... A01H 5/00

(52) U.S. Cl. ..... Plt./288

(58) Field of Search ..... Plt./288, 287

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar characterized by large decorative type inflorescences, consistent flowering response to short days, blooming consistently after 49 days of short day length, free branching habit, and a consistent natural season flowering habit during the first two weeks of September.

1 Drawing Sheet

LATIN NAME

*Dendranthema morifolium.*

VARIETY

Figure 1:
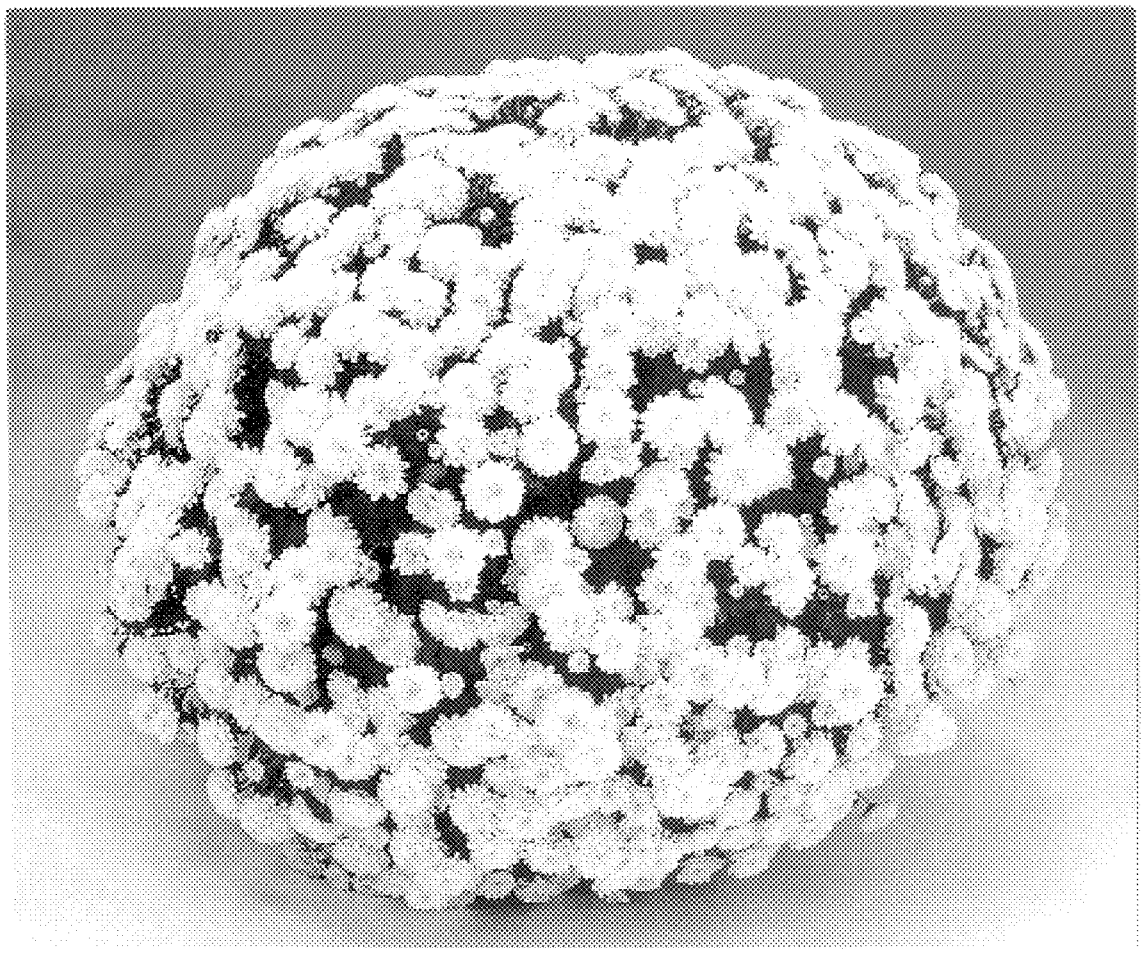

'GEDI ONE FRI'.

BACKGROUND OF THE INVENTION

The present invention relates to a new and distinct cultivar of Chrysanthemum plant, botanically known as *Dendranthema morifolium* and hereinafter referred to by the cultivar name 'GEDI ONE FRI.'

The new cultivar is a product of hybridization of the female parent 'GEDI WO' (U.S. Plant Pat. No. 12,259) and the male parent 'Speedo' (unpatented). The new cultivar was discovered and selected by the inventor in October 1997.

Asexual reproduction of the new cultivar by apical tip cutting and meristem tissue culture was performed in Oxnard, Calif. and has shown that the unique features of this new Chrysanthemum cultivar are stable and reproduced true to type on successive generations.

SUMMARY OF THE INVENTION

The cultivar 'GEDI ONE FRI' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE FRI.' These observations were made on plants approximately 130 days old from rooted cuttings. These characteristics in combination distinguish 'GEDI ONE FRI' as a new and distinct Chrysanthemum cultivar:

1. Large decorative type inflorescence;

2. Consistent flowering response to short days, blooming consistently after 49 days of short day length;

3. Free branching habit; and

4. Consistent natural season flowering habit during the first two weeks of September.

Plants of the new cultivar are similar to plants of the parent cultivars, 'Gedi WO' and 'Speedo' in most horticultural characteristics, however plants of the new cultivar differed from plants of the parent cultivars primarily in bloom characteristics. In comparisons of plants of the new cultivar with the parent cultivars the following characteristics differed:

1. The new cultivar has a wider diameter flower than cultivar 'Gedi WO;'

2. The new cultivar has many more ray florets than cultivar 'Gedi WO;'

3. The new cultivar naturally blooms three weeks earlier than the cultivar 'Gedi WO;'

4.The new cultivar has fully decorative flowers, while the cultivar 'Gedi WO' has daisy type flowers;

5. The new cultivar has a wider diameter flower than the cultivar 'Speedo;'

6. The new cultivar has many more ray florets than the cultivar 'Speedo;' and

7. The new cultivar naturally blooms three weeks earlier than the cultivar 'Speedo'.

BRIEF DESCRIPTION OF THE PHOTOGRAPHS

The photograph shows a plant of the new cultivar which was grown in a 2-gallon container. A single cutting was grown in the container, and the plant was grown in outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000. The growing conditions range from 60° to 65° F. at night to 70° to 85° F. during the day. Measurements and numerical values represent averages of typical flowering types.

Botanical classification: *Dendranthema morifolium* cultivar 'GEDI ONE FRI'.

Commercial classification: Garden-type Chrysanthemum.
Parentage: Hybridization of female parent 'Gedi WO' and male parent 'Speedo'.

PROPAGATION

Time to rooting: 7 to 14 days at approximately 21° C.
Root description: Fine, fibrous.

PLANT

Growth habit: Mounding herbaceous perennial.
Height: Approximately 28 cm.
Plant spread: Approximately 31 cm.
Growth rate: Moderate.
Branching characteristics: Free branching.
Internode length: Approximately 2.3 cm.

FOLIAGE

Leaf:
*Arrangement.*—Alternate, single.
*Average length.*—Aproximately 7.2 cm.
*Average width.*—Approximately 3.7 cm.
*Shape of blade.*—Ovate.
*Apex.*—Acuminate.
*Base.*—Attenuate.
*Attachment.*—Stalked.
*Margin.*—Pinnately lobed and toothed.
*Texture of top surface.*—Lightly pubescent.
*Texture of bottom surface.*—Lightly pubescent.
*Color.*—Young foliage upper side: Near 137A. Young foliage under side: Near 137B. Mature foliage upper side: Near 137A. Mature foliage under side: Near 137B. Venation upper side: Near 138C. Venation under side: Near 137C.

Petiole:
*Average length.*—Approximately 2.3 cm
*Color.*—Near 138A
*Diameter.*—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the last two weeks in September.
*Number of inflorescences per stem.*—Approximately 11.
*Infloresence diameter.*—Approximately 6 cm.
*Inflorescence depth.*—1.5 cm.
*Inflorescence longevity on plant.*—Approximately 22–26 days
*Persistence.*—Persistent.

Ray florets:
*Appearance.*—Matte.
*Texture.*—Smooth.
*Average number per flower.*—250.
*Shape.*—Oblanceolate.
*Margin.*—Entire.
*Apex.*—Obtuse.
*Length.*—Approximately 3.5 cm.
*Width.*—Approximately 0.8 cm.
*Color.*—Upper surface at first opening: Near 18B. Upper surface at maturity: Near 158D. Upper surface at fading: Near 155B. Under surface at first opening: Near 18C. Under surface at maturity: Near 158D. Under surface at fading: Near 155B. Center ray florets color: Near 13D at maturity and fading.

Disc florets:
*Appearance.*—Shiny.
*Texture.*—Smooth.
*Average number per flower.*—Approximately 40.
*Shape.*—Cylindric.
*Apex.*—Obtuse.
*Average length.*—Approximately 1 cm.
*Average width.*—Approximately 0.2 cm.
*Color.*—At first opening: Near 2A. At maturity: Near 16B. At fading: Near 17D.

Peduncle:
*Length.*—At terminal end (shortest): Approximately 5 cm. At lateral end (longest): Approximately 9 cm.
*Diameter.*—Approximately 0.3 cm.
*Strength.*—Moderate.
*Color.*—Near 137C.
*Habit.*—Erect.
*Surface texture.*—Lightly pubescent.

Inflorescence bud:
*Length.*—Approximately 1 cm.
*Diameter.*—Approximately 1 cm.
*Form.*—Globular.
*Color.*—Near 16C.

Phyllaries:
*Appearance.*—Matte.
*Texture.*—Lightly pubescent.
*Number.*—Aproximately 40 to 50.
*Shape.*—Ovate.
*Margin.*—Entire.
*Apex.*—Acute.
*Diameter.*—Approximately 0.2 cm.
*Length.*—Approximately 0.5 cm.
*Color.*—Upper side: Near 137A. Under side: Near 137A.

REPRODUCTIVE ORGANS

Ray florets:
*Number of pistils per flower.*—1.
*Stigma shape.*—2 branched.
*Stigma color.*—Near 16D.
*Style color.*—Near 16D.
*Style length.*—0.6 cm.
*Stamens.*—Absent.

Disc florets:
*Number of pistils per flower.*—1.
*Stigma shape.*—Cylindric.
*Style length.*—0.5 cm.
*Number of stamens per flower.*—Approximately 5.
*Anther shape.*—Tubular.
*Anther color.*—Near 16A.
*Pollen color.*—Near 17B.

OTHER CHARACTERISTICS

Seed production: Commercially, this plant is not used or observed in a stage wherein seeds would be produced. Therefore, seed production has not been observed.
Flower fragrance: Absent.

What is claimed is:

1. A new and distinct cultivar of Chrysanthemum plant named 'GEDI ONE FRI' as herein illustrated and described.

* * * * *